United States Patent
Lin

(10) Patent No.: US 8,784,555 B2
(45) Date of Patent: Jul. 22, 2014

(54) SURFACE ACTIVE BLOCKED ISOCYANATES AND COATING COMPOSITIONS THEREOF

(75) Inventor: Jun Lin, Troy, MI (US)

(73) Assignee: Axalta Coating Systems IP Co., LLC, Wilmington, DE (US)

( * ) Notice: Subject to any disclaimer, the term of this patent is extended or adjusted under 35 U.S.C. 154(b) by 220 days.

(21) Appl. No.: 13/054,828

(22) PCT Filed: Jul. 23, 2009

(86) PCT No.: PCT/US2009/051554
§ 371 (c)(1),
(2), (4) Date: Jan. 19, 2011

(87) PCT Pub. No.: WO2010/014494
PCT Pub. Date: Feb. 4, 2010

(65) Prior Publication Data
US 2011/0120344 A1    May 26, 2011

Related U.S. Application Data

(60) Provisional application No. 61/084,346, filed on Jul. 29, 2008.

(51) Int. Cl.
*C09D 7/00* (2006.01)
*C07F 7/18* (2006.01)

(52) U.S. Cl.
CPC .... *C09D 7/00* (2013.01); *C07F 7/18* (2013.01)
USPC ...................... 106/287.11; 548/110

(58) Field of Classification Search
CPC .................................. C09D 7/00; C07F 7/18
USPC ...................... 106/287.11; 548/110
See application file for complete search history.

(56) References Cited

U.S. PATENT DOCUMENTS

| 5,384,367 | A | | 1/1995 | Swarup et al. |
| 5,583,244 | A | * | 12/1996 | Uchida et al. ............... 556/419 |
| 5,986,033 | A | | 11/1999 | Hughes et al. |
| 6,300,414 | B1 | | 10/2001 | McGee et al. |
| 6,592,998 | B2 | | 7/2003 | Anderson et al. |
| 6,592,999 | B1 | | 7/2003 | Anderson et al. |
| 6,623,791 | B2 | | 9/2003 | Sadvary et al. |
| 7,144,631 | B2 | | 12/2006 | Lin et al. |
| 7,329,468 | B2 | | 2/2008 | Anderson et al. |
| 2003/0072943 | A1 | | 4/2003 | Anderson et al. |
| 2004/0075161 | A1 | | 4/2004 | Wang et al. |
| 2006/0058488 | A1 | | 3/2006 | Kuhnle et al. |
| 2007/0083017 | A1 | | 4/2007 | Deuber et al. |
| 2008/0076876 | A1 | | 3/2008 | Menovick et al. |

FOREIGN PATENT DOCUMENTS

| EP | 1036827 A2 | 9/2000 | |
| EP | 1806385 A1 | 7/2007 | |
| JP | 59086612 A * | 5/1984 | ............. C08F 30/08 |
| WO | 2004046156 A1 | 6/2004 | |

OTHER PUBLICATIONS

ISA Korean Intellectual Property Office, International Search Report and Written Opinion for Application No. PCT/US2009/051554, dated Mar. 9, 2010.
ISA Korean Intellectual Property Office, International Preliminary Report on Patentability for Application No. PCT/US2009/051554, dated Feb. 1, 2011.
SIPO, Chinese Office Action for Application No. 200980129814, dated Dec. 19, 2012.

\* cited by examiner

*Primary Examiner* — Joseph Kosack
(74) *Attorney, Agent, or Firm* — Ingrassia Fisher & Lorenz, P.C.

(57) ABSTRACT

Disclosed herein is a surface active adhesion promoting agent and a coating composition comprising the surface active adhesion promoting agent. The adhesion promoting agent is a blocked isocyanate functional siloxane containing material. Addition of small amount of the adhesion promoting agent to a coating composition, especially clearcoat compositions, helps to provide adhesion to a variety of materials that may be subsequently applied to the coating composition.

9 Claims, No Drawings

SURFACE ACTIVE BLOCKED ISOCYANATES AND COATING COMPOSITIONS THEREOF

FIELD OF THE DISCLOSURE

A coating composition comprising an adhesion promoting agent is disclosed that has good Motor Vehicle Safety Standard (MVSS) adhesion to non-silanated urethane sealers. The disclosed coating composition also has good adhesion to repair coatings, bed liners and other compositions that are subsequently applied.

DESCRIPTION OF THE RELATED ART

The use of clearcoat finishes over a basecoat is well-known in the painting of vehicles. Many different types of clearcoats have been developed over the years. It is known in the art to use clearcoats that contain silane functionality for resistance to environmental etch damage, such as the etching caused by acid rain. Many of these silane containing clearcoats are commercially available and in wide spread use today. However, silane containing clearcoats also have a low surface energy which presents a challenge to repair damaged portions of the clearcoat. These silane containing clearcoats are also difficult to achieve MVSS adhesion to windshields which are important for the structural integrity of the vehicle.

In conventional windshield bonding operations at a vehicle assembly plant, the windshield is affixed to the body of a vehicle which has already been painted with a basecoat/clearcoat finish. During this process, a bead of moisture-cure sealant material is applied along the windshield frame over the previously cured basecoat/clearcoat finish. The windshield sealant is expected to adhere to the basecoat/clearcoat finish to hold the windshield in place and meet current MVSS and automobile manufacturer regulations.

Silane containing clearcoats present the sealant material a challenge to providing the necessary level of adherence. Several solutions have been developed to overcome the problems of adhering to silane containing clearcoats. One approach to the problem is to provide a sealant composition that contains catalysts that promote a reaction between the sealant composition and the components in the clearcoat. Another approach is to place a primer composition over top of the clearcoat layer in the area where the windshield will contact the vehicle frame. The primer composition provides the necessary sealant adhesion. Alternatively, silane functional molecules can be added to the sealant composition to provide the required good adhesion.

Another approach to achieve good adhesion is to add an adhesion promoting boric acid or boric acid equivalent to a coating composition along with an agent that promotes the migration of the adhesion promoter to the surface layer of the applied coating, such as, for example, a siloxane functional compound. The adhesion promoter and the agent that promotes migration to the surface are reacted with one another either prior to being added to the coating composition or they are added as separate components that will react with one another during the curing stage. The reaction product of these two agents is a polysiloxane borate. Comparative examples show that if the boron component is not present, then adhesion between the applied layers is poor.

While these approaches produce the desired solution, there is a continuing need for advances that improve the performance and other shortcomings of the currently known products.

SUMMARY OF THE DISCLOSURE

The current disclosure teaches a surface active adhesion promoting agent comprising at least a blocked isocyanate and a siloxane portion having at least two or more silicone atoms and a number average molecular weight in the range of from 500 to 4500.

In another embodiment, the disclosure relates to a surface active adhesion promoting agent wherein the surface active adhesion promoting agent is of the formula;

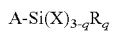

wherein q is 0, 1 or 2;
A is $G-C(O)NH-R^1$ and is attached to the silicon atom through $R^1$;
G is the residue of an isocyanate blocking agent;
each X is independently chosen from the group consisting of $OR^2$, OY, $OSi(X')_2A$ or a hydrolysable group; wherein at least one of X is OY or $OSi(X')_2A$;
Y is $Si(Z)_{3-w}(R^3)_w$ or $Si(X')_2A$;
each X' is independently chosen from the group consisting of $OR^2$, OY or a hydrolysable group;
each Z is independently chosen from the group consisting of $OR^4$, $OSi(X')_2A$, OY, hydrolysable group or a silsesquioxane;
$R^1$ is a divalent organic radical having from 1 to 20 carbon atoms;
each R, $R^2$, $R^3$ or $R^4$ is independently chosen from the group consisting of C1 to C8 aliphatic group, C3 to C20 cycloaliphatic, alkylcycloaliphatic, cycloaliphaticalkyl group, C6 to C20 aryl group or a fluorine containing or perfluoro derivative thereof;
w is 0, 1 or 2; and
wherein $A-Si(X)_{3-q}R_q$ has a molecular weight in the range of from 500 to 4500.

The current disclosure also relates to a coating composition comprising a surface active adhesion promoting agent wherein the surface active adhesion promoting agent is of the formula;

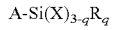

wherein q is 0, 1 or 2;
A is $G-C(O)NH-R^1$ and is attached to the silicon atom through $R^1$;
G is the residue of an isocyanate blocking agent;
each X is independently chosen from the group consisting of $OR^2$, OY, $OSi(X')_2A$ or a hydrolysable group; wherein at least one of X is OY or $OSi(X')_2A$;
Y is $Si(Z)_{3-w}(R^3)_w$ or $Si(X')_2A$;
each X' is independently chosen from the group consisting of $OR^2$, OY or a hydrolysable group;
each Z is independently chosen from the group consisting of $OR^4$, $OSi(X')_2A$, OY, hydrolysable group or a silsesquioxane;
$R^1$ is a divalent organic radical having from 1 to 20 carbon atoms;
each R, $R^2R^3$ or $R^4$ is independently chosen from the group consisting of C1 to C8 aliphatic group, C3 to C20 cycloaliphatic, alkylcycloaliphatic, cycloaliphaticalkyl group, C6 to C20 aryl group or a fluorine containing or perfluoro derivative thereof;
w is 0, 1 or 2; and
wherein $A-Si(X)_{3-q}R_q$ has a molecular weight in the range of from 500 to 4500.

DETAILED DESCRIPTION

The features and advantages of the present disclosure will be more readily understood, by those of ordinary skill in the art, from reading the following detailed description. It is to be appreciated that certain features of the disclosure, which are, for clarity, described above and below in the context of separate embodiments, may also be provided in combination in a single embodiment. Conversely, various features of the disclosure that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. Also, the disclosure of these ranges is intended as a continuous range including every value between the minimum and maximum values.

As used herein, the term "surface active" means that a particular component tends to migrate toward the surface of an applied, but uncured, layer of a coating composition. When a coating composition containing a surface active ingredient is applied to a substrate, the surface active ingredient will migrate towards the surface that is away from the substrate side of the applied layer. While not all of the surface active material will be present at the surface, the applied layer will have a graduated concentration of the surface active ingredient with a relatively higher concentration at the surface opposite the substrate layer and a relatively lower concentration of the surface active ingredient closer to the substrate to which the layer was applied.

As used herein, the term "substantially free from boron" means that the coating composition has less than 0.001 weight percent of elemental boron based on the total weight of the resin solids. In one embodiment, no boron containing compounds are added to the composition. It is possible, that some of the ingredients added to the coating composition may contain small amounts of boron. These minor amounts of boron should be minimized wherever possible, and it is not the purpose of any embodiment to add any boron containing compounds to the coating composition.

A surface active adhesion promoting agent, also called an adhesion promoting agent, has been found that helps to improve the adhesion of a clearcoat to commonly applied windshield sealants and also provides recoat adhesion. The adhesion promoting agent is a silane functional blocked isocyanate and is added to the clearcoat composition. It is especially useful for providing the requisite adhesion between a cured layer of clearcoat and a windshield sealant or a repair coating applied over the cured clearcoat. According to the present disclosure, the adhesion promoting agent comprises or consists essentially of the silane functional blocked isocyanate.

In one embodiment, the surface active adhesion promoting agent comprises or consists essentially of a compound containing at least a blocked isocyanate and a siloxane portion having at least two or more silicone atoms and a number average molecular weight in the range of from 500 to 4500. By blocked isocyanate is meant that an isocyanate functional group is reacted with a moiety that is reactive with the isocyanate functional group so as to form a urea or urethane functional group. During the reaction to form the blocked isocyanate it is intended to block all of the isocyanate groups that will form a part of the adhesion promoting agent. However, it is possible that a certain portion of the isocyanate groups may remain unblocked. The portion of unblocked isocyanate groups should remain as small as is possible under a given set of reaction conditions.

In another embodiment, the surface active adhesion promoting agent comprises or consists essentially of a silane functional blocked isocyanate having a formula according to structure (I);

$$A\text{-}Si(X)_{3-q}R_q \quad (I)$$

wherein q is 0, 1 or 2; A is G-C(O)NH—$R^1$ and is attached to the silicon atom through $R^1$;

G is the residue of an isocyanate blocking agent;

each X is independently chosen from the group consisting of $OR^2$, OY, $OSi(X')_2A$ or a hydrolysable group; wherein at least one of X is OY or $OSi(X')_2A$;

Y is $Si(Z)_{3-w}(R^3)_w$ or $Si(X')_2A$;

each X' is independently chosen from the group consisting of $OR^2$, OY or a hydrolysable group;

each Z is independently chosen from the group consisting of $OR^4$, $OSi(X')_2A$, OY, a hydrolysable group or a silsesquioxane;

$R^1$ is a divalent organic radical having from 1 to 20 carbon atoms;

each R, $R^2$, $R^3$ or $R^4$ is independently chosen from the group consisting of optionally substituted C1 to C8 aliphatic group, optionally substitute C3 to C20 cycloaliphatic, optionally substituted C6 to C20 aryl group or a fluorine containing or perfluoro derivative thereof;

w is 0, 1 or 2; and wherein $A\text{-}Si(X)_{3-q}R_q$ has a number average molecular weight in the range of from 500 to 4500.

In another embodiment, the surface active adhesion promoting agent is a silane functional blocked isocyanate having a formula according to structure (I);

$$A\text{-}Si(X)_{3-q}R_q \quad (I)$$

wherein q is 0, 1 or 2; A is G-C(O)NH—$R^1$ and is attached to the silicon atom through $R_1$;

G is the residue of an isocyanate blocking agent;

each X is independently chosen from the group consisting of $OR^2$, OY, $OSi(X')_2A$ or a hydrolysable group; wherein at least one of X is OY or $OSi(X')_2A$;

Y is $Si(Z)_{3-w}(R^3)_w$ or $Si(X')_2A$;

each X' is independently chosen from the group consisting of $OR^2$, OY or a hydrolysable group;

each Z is independently chosen from the group consisting of $OR^4$, $OSi(X')_2A$, OY, a hydrolysable group or a silsesquioxane;

$R^1$ is a divalent organic radical having from 1 to 20 carbon atoms;

each R, $R^2$, $R^3$ or $R^4$ is independently chosen from the group consisting of optionally substituted C1 to C8 aliphatic group, optionally substitute C3 to C20 cycloaliphatic, optionally substituted C6 to C20 aryl group or a fluorine containing or perfluoro derivative thereof;

w is 0, 1 or 2; and wherein $A\text{-}Si(X)_{3-q}R_q$ has a number average molecular weight in the range of from 500 to 4500.

In any of the above embodiments, the surface active adhesion promoting agent is substantially free from boron.

In one embodiment, structure (I) can be produced, in two steps, by the reaction of an isocyanate functional silane compound, for example, gamma-isocyanatopropyl trimethoxy silane with a blocking agent such as dimethylpyrazole to form a silane functional blocked isocyanate. In the second step, the blocked isocyanate is then further reacted under hydrolysis conditions with itself, an alkyl trialkoxysilane, a dialkyl dialkoxysilane or a combination thereof. The hydrolysis conditions are chosen such that the number average molecular weight of the product is in the range of from 500 to 4500. Other methods for producing compounds of structure (I) are available to one of ordinary skill in the art.

The final product from this reaction sequence can be a mixture of many different products. The reaction can form linear structures, branched structures or under certain hydrolysis conditions, may contain silsesquioxane type structures. Examples of structure (I) include, but are not limited to, any of the structures listed below as (II), (III), (IV) or (V). These structures represent a sampling of the structures that can be possible when gamma-isocyanatopropyl trimethoxy silane is first blocked with dimethylpyrazole and then reacted, under hydrolysis conditions, with methyl trimethoxysilane. These structures are meant to provide a sample of the possible compounds that can be produced from this reaction.

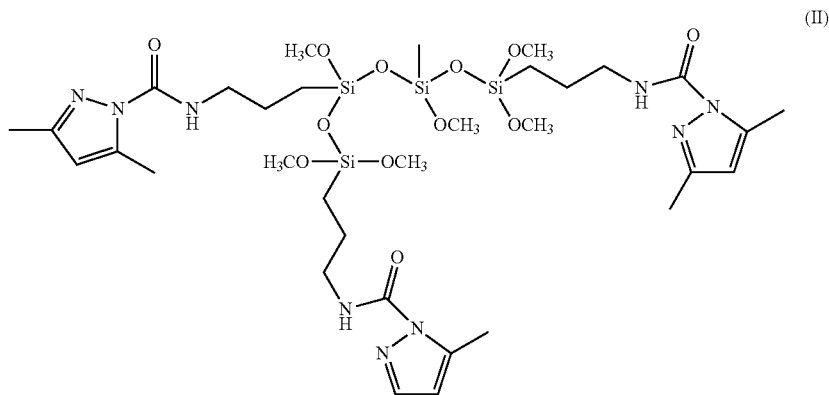

(II)

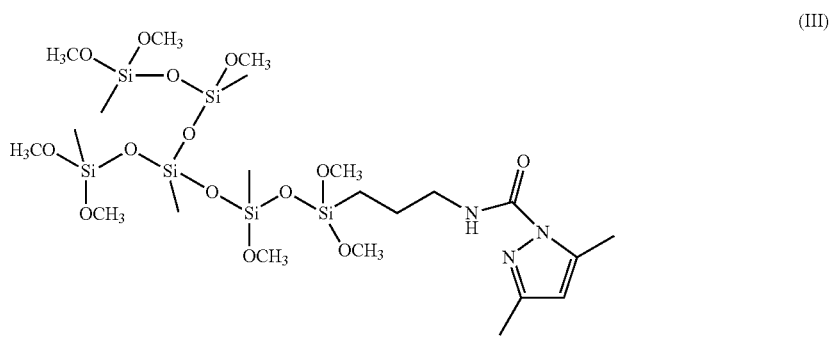

(III)

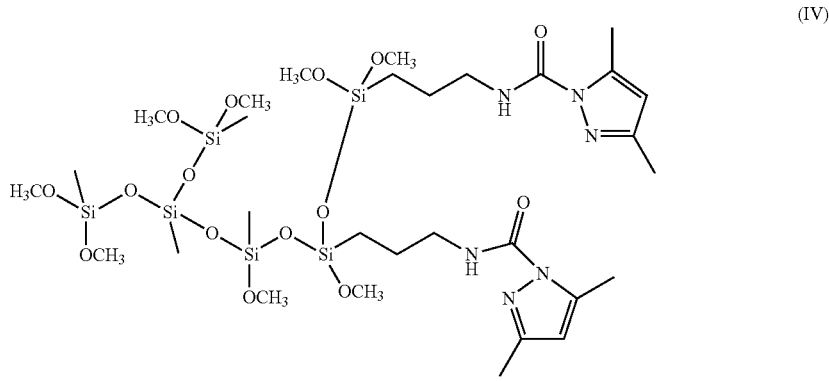

(IV)

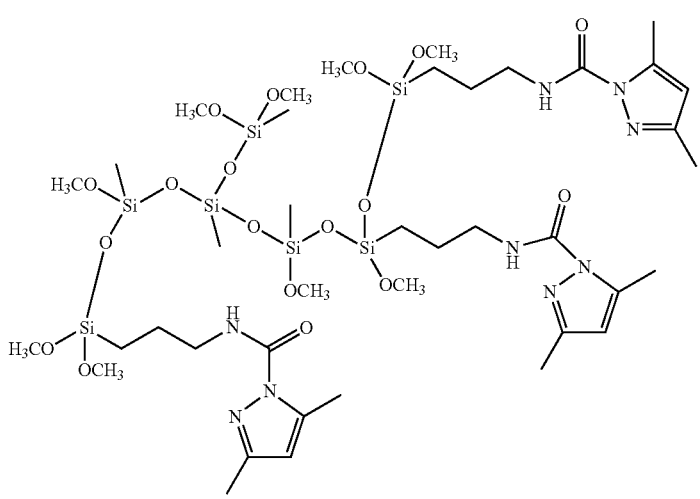

(V)

The self condensation of the silane functional blocked isocyanate can occur when the silane functional blocked isocyanate is hydrolyzed without an alkoxy trialkoxysilane or a dialkyl dialkoxysilane being present or it can occur during the hydrolysis reaction when an alkyl trialkoxysilane, a dialkyl dialkoxysilane or a combination thereof is present. The self condensation of the silane functional blocked isocyanate results in products such as, for example, that of (VI) and (VII). It should be noted that these structures are only representative and are not inclusive of every possibility;

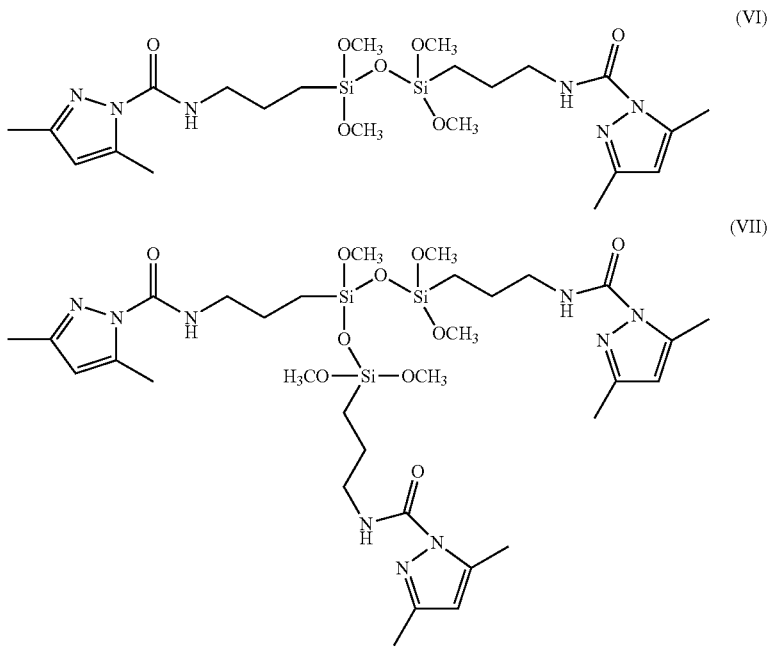

Suitable isocyanate functional silane compounds can be, for example, of the formula (VIII);

(VIII)

wherein q is 0, 1 or 2; each X is independently chosen from the group consisting of $OR^2$ or other hydrolyzable group; $R^1$ is a divalent radical having from 1 to 20 carbon atoms; and each R and $R^2$ is chosen from the group consisting of optionally substituted C1 to C8 aliphatic group, optionally substitute C3 to C20 cycloaliphatic, optionally substituted C6 to C20 aryl group or a fluorine containing or perfluoro derivative thereof.

Suitable examples include, for example, gamma-isocyanatopropyl trimethoxy silane, gamma-isocyanatopropyl triethoxy silane, gamma-isocyanatobutyl trimethoxy silane, gamma-isocyanatobutyl triethoxy silane or a combination thereof.

The isocyanate functionality can be blocked with many of the known blocking agents. In one embodiment, blocking agents can include heterocycles, such as, for example, pyrazoles, 3,5-dimethylpyrazole, imidazole, 2-methyl imidazole, 4-methyl imidazole, pyrroles, pyrrolidines, morpholines, pyridine, piperidines; alkyl malonates; acetoacetic esters and cyanoacetic esters having in each case 1 to 4 carbon atoms in the ester group; and NH-acidic compounds such as caprolactam. Combinations of the above blocking agents can be used as well. In one embodiment, the blocking agent is a heterocyclic compound and in another embodiment, the blocking agent is dimethylpyrazole.

The isocyanate blocking step can performed in the presence or absence of solvent. Solvents, if used, are typically organic solvents such as, for example, ethyl acetate, butyl acetate, methyl acetate, tert-butyl acetate, acetone, methyl ethyl ketone, methyl amyl ketone, petroleum ether, SOLVESSO® solvents available from ExxonMobil Chemicals, Houston, Tex.; aliphatic hydrocarbons such as, for example, heptane, hexane, cyclohexane; aromatic solvents, such as, for example, benzene, toluene, xylene, ethyl benzene; or a combination thereof.

A catalyst can optionally be used to help promote the reaction between the blocking agent and the isocyanate. Such catalysts include tin catalysts, for example, dibutyl tin dilaurate, dibutyl tin diacetate, monoalkyl tins, trialkyl tins or a combination thereof. Isocyanate blocking processes are well-known to those of ordinary skill in the art.

In one embodiment, the blocked isocyanate can then be reacted, under hydrolysis conditions, with a silane containing material having the structure according to (IX);

wherein Z is a hydrolysable group and $R^3$ is independently chosen from the groups consisting of optionally substituted C1 to C8 aliphatic group, optionally substitute C3 to C20 cycloaliphatic, optionally substituted C6 to C20 aryl group or a fluorine containing or perfluoro derivative thereof; and wherein n is 1 or 2. Combinations of any of the above silane containing materials can be used.

In one embodiment, the hydrolysis is done in the presence of water and optionally, an acidic catalyst can be added to the reaction to help accelerate the hydrolysis. Solvents are optional. Some suitable acid catalysts include aromatic sulfonic acids, such as, dodecylbenzene sulfonic acid, para-toluenesulfonic acid and dinonylnaphthalene sulfonic acid. Other acid catalysts that can be used, such as phosphoric acids, more particularly, phenyl acid phosphate, benzoic acid, oligomers having pendant acid groups. Combinations thereof can also be used.

As was mentioned, the product of this reaction will, in general, be a mixture of several products, and can include those products wherein several silane functional groups have joined together to form a silsesquioxane type structure having ring or cage structures. The number average molecular weight of the product should be in the range of from 500 to 4500.

The adhesion promoting agent according to the present disclosure is particularly suited to be used in a silane containing clearcoat composition. Such silane containing clearcoat compositions often have low adhesion to a windshield sealant composition that does not contain silane or does not have large amounts of catalyst to promote adhesion and will often fail the Motor Vehicle Safety Standards that require the windshield to remain in place in the event of an accident. In addition such silane containing clearcoats are often difficult to repair as the repair coating compositions often have poor adhesion to cured silane containing clearcoats.

In one embodiment, a coating composition is disclosed comprising a surface active adhesion promoting agent wherein the surface active adhesion promoting agent comprises or consists essentially of a compound containing at least a blocked isocyanate and a siloxane portion having at least two or more silicone atoms and the compound has a number average molecular weight in the range of from 500 to 4500.

In another embodiment, is disclosed a coating composition comprising a surface active adhesion promoting agent wherein the adhesion promoting agent comprises or consists essentially of a silane functional blocked isocyanate having a formula according to structure (I);

wherein q is 0, 1 or 2; A is $G-C(O)NH-R^1$ and is attached to the silicon atom through $R_1$;

G is the residue of an isocyanate blocking agent;

each X is independently chosen from the group consisting of $OR^2$, OY, $OSi(X')_2A$ or a hydrolysable group; wherein at least one of X is OY or $OSi(X')_2A$;

Y is $Si(Z)_{3-w}(R^3)_w$ or $Si(X')_2A$;

each X' is independently chosen from the group consisting of $OR^2$, OY or a hydrolysable group;

each Z is independently chosen from the group consisting of $OR^4$, $OSi(X')_2A$, OY, a hydrolysable group or a silsesquioxane;

$R^1$ is a divalent organic radical having from 1 to 20 carbon atoms;

each R, $R^2$, $R^3$ or $R^4$ is independently chosen from the group consisting of optionally substituted C1 to C8 aliphatic group, optionally substitute C3 to C20 cycloaliphatic, optionally substituted C6 to C20 aryl group or a fluorine containing or perfluoro derivative thereof;

w is 0, 1 or 2; and wherein $A-Si(X)_{3-q}R_q$ has a number average molecular weight in the range of from 500 to 4500.

In another embodiment, the coating composition is substantially free from boron.

The addition of relatively small amounts of the adhesion promoting agent to a silane containing clearcoat composition improves the adhesion of the non-silane windshield sealant to the cured clearcoat and that of repair coating compositions. In one embodiment, the adhesion promoting agent can be added in amounts in the range of from 0.5 percent to 7 percent by weight based on the total weight of binder components in the clearcoat composition. The adhesion promoting agent can be used at amounts of greater than 7 percent by weight, however, in practice, additional amounts added to the composition do not improve the already superior adhesion. The adhesion promoting agent is typically added until the point where the sealant material passes all required adhesion tests or a slight excess beyond that point is added. By total weight of binder components is meant the total weight of only those components that form a part of the crosslinked clearcoat network. Additives such as solvents, light stabilizers, anti-oxidants, rheology control agents are not included in this definition.

Suitable silane containing clearcoat compositions are known in the art and include GEN IV® ES and GEN V® clearcoats available from DuPont, Wilmington, Del. Suitable clearcoat compositions include binder components that contain silane functional acrylic polymers, known as acrylosilanes; silane functional polyesters; silane functional polyurethanes or combinations thereof. The clearcoats are typically crosslinked, and the crosslinking agent can be melamine or other amino resins that are well-known in the art; blocked or unblocked polyisocyanates; or any combinations thereof. The blocked polyisocyanates that are mentioned as crosslinking agents are intended to be different than the blocked isocyanate of the adhesion promoting agent.

While the adhesion promoting agent is especially useful in a clearcoat composition containing silane functional groups, it is not limited to only silane clearcoat compositions. Adding the adhesion promoting agent to non-silane clearcoats can also help to improve the adhesion of the windshield sealant and the recoat adhesion to the clearcoat composition.

Addition of the adhesion promoting agent to coating compositions can help to improve the adhesion of the coating composition to subsequently applied layers. In general, the subsequently applied layers will have excellent adhesion when they contain functional groups that are able to react with the blocking agent, the isocyanate and/or the silane components of the adhesion promoting agent. Suitable subsequently applied layers can include, for example, bed liners, repair coatings, sealant materials, sound deadening layers, or adhesive compositions.

The adhesion promoting agent can be added to clearcoat compositions, simply by mixing and stirring to disperse the agent. Optionally, the mixture can then be reduced with a suitable solvent to the desired viscosity for application.

Application of the coating composition comprising the adhesion promoting agent is by known methods. Suitable applications methods include, for example, electrostatic spraying, pneumatic spraying, roller coating, flow coating, dip coating or brushing. Any of the application methods can be done using either manual or automatic methods as is common in the art.

The clearcoat composition containing the adhesion promoting agent can be applied to a variety of substrates. In one embodiment, the clearcoat composition is applied to an automobile during its manufacture. In this application, a multilayer coating is formed on the vehicle comprising one or more of an electrocoat layer, a primer layer, and a basecoat layer. In a typical application process, a metal substrate is coated by dipping into an electrocoat bath. This electrocoat layer is cured by baking. One or more layers of a primer can then be applied to help to smooth the electrocoat layer and to provide a chip resistant undercoat layer. The primer layer can optionally flashed to remove at least a portion of the solvent and/or baked to provide a cured layer of primer. To the primer layer, one or more layers of a basecoat can be applied which will provide the desired color range of the substrate. The applied basecoat layer is generally flashed to remove at least a portion of the solvent. Optionally, the basecoat can be baked. One or more layers of the clearcoat composition comprising the adhesion promoting agent can then be applied. The applied clearcoat layers can be optionally flashed and cured to provide a finish for the substrate.

During the manufacturing of an automobile, the windshield is attached to the vehicle after the applied clearcoat has been cured, typically by baking. A bead of windshield sealant is applied to the frame portion of the vehicle that will receive the windshield. The windshield is then set into place and the sealant is allowed to cure. The sealant is typically a moisture cure sealant, although other cure methods are known and can be used.

Typical substrates for the clearcoat composition comprising the adhesion promoting agent include, for example, automotive vehicles, automobile bodies, any and all items manufactured and painted, such as, for example, frame rails, commercial trucks and truck bodies, including but not limited to beverage bodies, utility bodies, ready mix concrete delivery vehicle bodies, waste hauling vehicle bodies, and fire and emergency vehicle bodies, as well as any potential attachments or components to such truck bodies, buses, farm and construction equipment, truck caps and covers, commercial trailers, consumer trailers, recreational vehicles, including but not limited to, motor homes, campers, conversion vans, vans, pleasure vehicles, pleasure craft snow mobiles, all terrain vehicles, personal watercraft, motorcycles, boats, and aircraft. The substrate further includes industrial and commercial new construction and maintenance thereof; walls of commercial and residential structures, such office buildings and homes; amusement park equipment; marine surfaces; outdoor structures, such as bridges, towers; coil coating; railroad cars; machinery; OEM tools; signage; sporting goods; and sporting equipment. The substrates can have any shape, for example, in the form of automotive body components, such as bodies (frames), hoods, doors, fenders, bumpers and/or trim, for automotive vehicles.

EXAMPLES

The following ingredients are available, at the time of this application, from the following manufacturers. Unless otherwise specified, all ingredients are available from the Aldrich Chemical Company, Milwaukee, Wis.

Gamma-isocyanatopropyl trimethoxy silane is available as SILQUEST® A-Link 35, from GESilicones, Wilton, Conn.

GEN IV® Silane Clearcoat, 648A01175 Ebony basecoat, 554-DN082 Primer Surface, and ED 5050 Electrocoat compositions are all available from DuPont, Wilmington, Del.

DESMODUR® VP LS2352 blocked isocyanate is available from Bayer material Sciences, Pittsburgh, Pa.

F503 Windshield sealant is available from EFTEC North America, LLC., Troy, Mich.

All gas permeation chromatography (GPC) was performed using an HP gas chromatograph, available from Agilent, Santa Clara, Calif., using tetrahydrofuran as the solvent and polystyrene as a standard.

Preparation of Silane Functional Blocked Isocvanates 1 and 2

Preparation of Silane Functional Blocked Isocyanate #1

15 grams of butyl acetate, 12.9 grams of 3,5-dimethylpyrazole (DMP) and 26.1 grams of gamma-isocyanatopropyl trimethoxy silane was added to a 60 ml glass bottle with stirring. The mixture was stirred until an exothermic reaction occurred. The reaction was then heated at 60° C. for 16 hours. The reaction was then cooled to room temperature and FT-IR analysis showed the absence of the isocyanate absorption band at 2278 $cm^{-1}$. The resulting solution had a solids content of 72%.

Preparation of Silane Functional Blocked Isocyanate #2

15 grams of butyl acetate, 9.2 grams of imidazole and 26.1 grams of gamma-isocyanatopropyl trimethoxy silane was added to a 60 ml glass bottle with stirring. The mixture was stirred until an exothermic reaction occurred. The reaction was then heated at 60° C. for 16 hours. The reaction was then cooled to room temperature and FT-IR analysis showed the absence of the isocyanate absorption band at 2278 $cm^{-1}$. The resulting solution had a solids content of 70%.

Preparation of Surface Active Blocked Isocyanates

Preparation of Surface Active Blocked Isocyanate #1

30 grams of silane functional blocked isocyanate #1, 1.9 grams of deionized water and 0.09 grams of phenyl acid phosphate was added to a 60 ml bottle with stirring. The mixture was stirred for several minutes until a clear solution was formed. The mixture was then stirred at 60° C. for 15 hours. GPC analysis showed a weight average molecular weight of 3904, a number average molecular weight of 2691 and a polydispersity of 1.47.

Preparation of Surface Active Blocked Isocyanate #2

30 grams of silane functional blocked isocyanate #1, 21.6 grams of methyl trimethoxysilane, 3.9 grams of deionized water and 0.18 grams of phenyl acid phosphate was added to a 60 ml bottle with stirring. The mixture was stirred for several minutes until a clear solution was formed. The mixture was then stirred at 60° C. for 15 hours. GPC analysis showed a weight average molecular weight of 2271, a number average molecular weight of 1452 and a polydispersity of 1.56.

Preparation of Surface Active Blocked Isocyanate #3

30 grams of silane functional blocked isocyanate #1, 21.6 grams of methyl trimethoxysilane, 5.3 grams of deionized water and 0.18 grams of phenyl acid phosphate was added to a 60 ml bottle with stirring. The mixture was stirred for several minutes until a clear solution was formed. The mixture was then stirred at 60° C. for 15 hours. GPC analysis showed a weight average molecular weight of 2623, a number average molecular weight of 1610 and a polydispersity of 1.63.

Preparation of Surface Active Blocked Isocyanate #4

30 grams of silane functional blocked isocyanate #1, 21.6 grams of methyl trimethoxysilane, 2.1 grams of deionized water and 0.18 grams of phenyl acid phosphate was added to a 60 ml bottle with stirring. The mixture was stirred for several minutes until a clear solution was formed. The mixture was then stirred at 60° C. for 15 hours. GPC analysis showed a weight average molecular weight of 1138, a number average molecular weight of 820 and a polydispersity of 1.39.

Preparation of Surface Active Blocked Isocyanate #5

30 grams of silane functional blocked isocyanate #1, 21.6 grams of dimethyl dimethoxysilane, 3.9 grams of deionized water and 0.18 grams of phenyl acid phosphate was added to a 60 ml bottle with stirring. The mixture was stirred for several minutes until a clear solution was formed. The mixture was then stirred at 60° C. for 15 hours. GPC analysis showed a weight average molecular weight of 2408 a number average molecular weight of 1553 and a polydispersity of 1.55.

Preparation of Surface Active Blocked Isocyanate #6

30 grams of silane functional blocked isocyanate #2, 21.6 grams of methyl trimethoxysilane, 3.9 grams of deionized water and 0.18 grams of phenyl acid phosphate was added to a 60 ml bottle with stirring. The mixture was stirred for several minutes until a clear solution was formed. The mixture was then stirred at 60° C. for 15 hours. GPC analysis showed a weight average molecular weight of 2603, a number average molecular weight of 785 and a polydispersity of 3.31.

Preparation of Clearcoat Examples

Clearcoat Example A (Control)

Clearcoat example A is GEN® IV silane clearcoat.

Preparation of Clearcoat Example B (Comparative)

10 grams of DESMODUR® VP LS2352 was added to 250 grams of GEN® IV silane clearcoat. The mixture was stirred for 30 minutes then reduced with 26 grams of ethyl-3-ethoxypropionate.

Preparation of Clearcoat Example C (Comparative)

6.5 grams of silane functional blocked isocyanate #1 was added to 250 grams of GEN® IV silane clearcoat. The mixture was stirred for 30 minutes then reduced with 25.6 grams of ethyl-3-ethoxypropionate.

Preparation of Clearcoat Example D 7.0 grams of surface active blocked isocyanate #1 was added to 250 grams of GEN® IV silane clearcoat. The mixture was stirred for 30 minutes then reduced with 25.7 grams of ethyl-3-ethoxypropionate.

Preparation of Clearcoat Example E 12.3 grams of surface active blocked isocyanate #2 was added to 250 grams of GEN® IV silane clearcoat. The mixture was stirred for 30 minutes then reduced with 25.7 grams of ethyl-3-ethoxypropionate.

Preparation of Clearcoat Example F 12.7 grams of surface active blocked isocyanate #3 was added to 250 grams of GEN® IV silane clearcoat. The mixture was stirred for 30 minutes then reduced with 26.3 grams of ethyl-3-ethoxypropionate.

Preparation of Clearcoat Example G 12.1 grams of surface active blocked isocyanate #4 was added to 250 grams of GEN® IV silane clearcoat. The mixture was stirred for 30 minutes then reduced with 26.2 grams of ethyl-3-ethoxypropionate.

Preparation of Clearcoat Example H 12.5 grams of surface active blocked isocyanate #1 was added to 250 grams of GEN® IV silane clearcoat. The mixture was stirred for 30 minutes then reduced with 26.2 grams of ethyl-3-ethoxypropionate.

Preparation of Clearcoat Example I 12.5 grams of surface active blocked isocyanate #1 was added to 250 grams of GEN® IV silane clearcoat. The mixture was stirred for 30 minutes then reduced with 26.2 grams of ethyl-3-ethoxypropionate.

Preparation of Clearcoat Example J 6.2 grams of surface active blocked isocyanate #1 was added to 250 grams of GEN® IV silane clearcoat. The mixture was stirred for 30 minutes then reduced with 25.6 grams of ethyl-3-ethoxypropionate.

Steel panels were prepared by electrocoating the panels with ED5050 electrocoating according to the manufacturers instructions. The electrocoated panels were then overcoated with 554-DN082 primer surfacer.

Procedure 1

Solventborne Ebony basecoat was applied to the primed panels. The panels were hand sprayed at 23° C. and 55% humidity in two coats allowing a 60 second flash off time between the first and second coat. The panel was flashed for 4 minutes following the application of the second basecoat. The clearcoat was applied to the panel in two spray passes allowing a 30 second flash time between the first and second application. After the second layer of clearcoat was applied, the panel was flashed for 10 minutes and baked in an oven at 60 minutes at 155° C. These panels were tested for recoat adhesion.

To test the recoat adhesion, the clearcoats were applied according to procedure 1. Within 24 hours of baking, the clearcoated panels were recoated with Ebony basecoat and the clearcoat compositions according to procedure 1, above. The panels were baked for 10 minutes at 135° C. The recoated panels were aged for a minimum of 24 hours and tested for recoat adhesion according to Method "B" of FLTM BI 106-01, published by the Ford Motor Company. The results of this test are shown in Table 1. For this test, a rating of 5% or less passes the test.

Procedure 2

For testing of the adhesion of windshield sealant, the solventborne Ebony basecoat was applied to the primed panels. The panels were hand sprayed at 23° C. and 55% humidity in two coats allowing a 60 second flash off time between the first and second coat. The basecoat was flashed for 4 minutes following the application of the second basecoat. The clearcoat was applied as to the panel as a wedge varying in thickness from 10 to 50 microns (dry film thickness) in two spray passes allowing a 30 second flash time between the first and second application. After the second layer of clearcoat composition was applied, the panel was flashed for 10 minutes and baked in an oven at 140° C. for 30 minutes. Within 12 hours of baking, a bead of F503 moisture cure windshield sealant, approximately 6 mm×6 mm×250 mm, was applied to each of the cured panels covering the wedge of clearcoat applied. The sealant was allowed to cure at 23° C. and 50% humidity for 72 hours and the adhesion was tested according to GM4352M and GM9522P specifications published by the General Motors Corporation. The desirable result is 100% cohesive failure (CF) of the adhesive beads, rather than a failure due to a loss of adhesion between the adhesive and the clearcoat or within the clearcoat or under layers. The areas which starts to show loss of adhesion between the adhesive and the clearcoat were measured for film builds. Generally, areas of low film builds of the clearcoat and high film build area of the basecoat would have a stronger tendency of losing adhesion of the adhesive beads due to migration of the clearcoat silane resin and basecoat catalyst between the two layers. The results for the cohesive failure are reported in Table 1. In this test, a rating of greater than 50% is considered to be acceptable, more preferably, a rating of 90% or better is desirable, and most preferably, a rating of greater than 95% is desired.

TABLE 1

| Clearcoat Example | Percentage blocked isocyanate* | MVSS adhesion (Cohesive Failure, CF) | Recoat adhesion |
|---|---|---|---|
| A (control) | 0 | 0% | <5% |
| B (comparison) | 5% | 0% | <5% |
| C (comparison) | 3% | 5% | <5% |

TABLE 1-continued

| Clearcoat Example | Percentage blocked isocyanate* | MVSS adhesion (Cohesive Failure, CF) | Recoat adhesion |
|---|---|---|---|
| D | 3% | 90% | <5% |
| E | 3% | 100% | <5% |
| F | 3% | 100% | <5% |
| G | 3% | 100% | <5% |
| H | 3% | 100% | <5% |
| I | 3% | 100% | <5% |
| J | 1.5% | 100% | <5% |

*as a percentage based on the total solids of the coating composition

What is claimed is:

1. A surface active adhesion promoting agent comprising at least a blocked isocyanate and a siloxane portion having at least two or more silicon atoms and a number average molecular weight in the range of from 500 to 4500, wherein said surface active adhesion promoting agent is of the formula;

$$A\text{-}Si(X)_{3-q}R_q$$

wherein q is 0, 1 or 2;

A is $G\text{-}C(O)NH\text{—}R^1$ and is attached to the silicon atom through $R^1$;

G is the residue of an isocyanate blocking agent;

each X is independently chosen from the group consisting of $OR^2$, OY, $OSi(X')_2A$ or a hydrolysable group; wherein at least one of X is OY or $OSi(X')_2A$;

Y is $Si(Z)_{3-w}(R^3)_w$ or $Si(X')_2A$;

each X' is independently chosen from the group consisting of $OR^2$, OY or a hydrolysable group;

each Z is independently chosen from the group consisting of $OR^4$, $OSi(X')_2A$, OY, hydrolysable group or a silsesquioxane;

$R^1$ is a divalent organic radical consisting of an alkyl group having from 3 to 4 carbon atoms;

each R, $R^2$, $R^3$ or $R^4$ is independently chosen from the group consisting of C1 to C8 aliphatic group, C3 to C20 cycloaliphatic, alkylcycloaliphatic, cycloaliphaticalkyl group, C6 to C20 aryl group or a fluorine containing or perfluoro derivative thereof;

w is 0, 1 or 2; and wherein $A\text{-}Si(X)_{3-q}R_q$ has a molecular weight in the range of from 500 to 4500.

2. The surface active adhesion promoting agent of claim 1 wherein each of R, $R^2$, $R^3$ or $R^4$ is $CH_3$.

3. The surface active adhesion promoting agent of claim 1 wherein the blocking agent is a pyrazole.

4. A coating composition comprising a surface active adhesion promoting agent wherein said surface active adhesion promoting agent comprises at least a blocked isocyanate and a siloxane portion having at least two or more silicon atoms and a number average molecular weight in the range of from 500 to 4500, wherein the surface active adhesion promoting agent is of the formula;

$$A\text{-}Si(X)_{3-q}R_q$$

wherein q is 0, 1 or 2;

A is $G\text{-}C(O)NH\text{—}R^1$ and is attached to the silicon atom through $R^1$;

G is the residue of an isocyanate blocking agent, wherein the blocking agent is chosen from the group selected from imidazole, 2-methyl imidazole, 4-methyl imidazole, pyrrole, pyrrolidine, morpholine, pyridine, piperidine, alkyl malonate, acetoacetic ester and cyanoacetic ester and a combination thereof;

each X is independently chosen from the group consisting of $OR^2$, OY, $OSi(X')_2A$ or a hydrolysable group; wherein at least one of X is OY or $OSi(X')_2A$;

Y is $Si(Z)_{3-w}(R^3)_w$ or $Si(X')_2A$;

each X' is independently chosen from the group consisting of $OR^2$, OY or a hydrolysable group;

each Z is independently chosen from the group consisting of $OR^4$, $OSi(X')_2A$, OY, hydrolysable group or a silsesquioxane;

$R^1$ is a divalent organic radical consisting of an alkyl group having from 3 to 4 carbon atoms;

each R, $R^2$, $R^3$ or $R^4$ is independently chosen from the group consisting of C1 to C8 aliphatic group, C3 to C20 cycloaliphatic, alkylcycloaliphatic, cycloaliphaticalkyl group, C6 to C20 aryl group or a fluorine containing or perfluoro derivative thereof;

w is 0, 1 or 2; and wherein $A$-$Si(X)_{3-q}R_q$ has a molecular weight in the range of from 500 to 4500.

5. The coating composition of claim 4, wherein said coating composition is substantially free from boron.

6. The coating composition of claim 4 wherein each of R, $R^2$, $R^3$ or $R^4$ is $CH_3$.

7. The coating composition of claim 4 wherein the isocyanate blocking agent is dimethylpyrazole.

8. The coating composition of claim 4, wherein the surface active adhesion promoting agent is present in an amount of 0.5 to 7 percent by weight based on the total weight of the binder components of said coating composition.

9. The coating composition of claim 4 wherein said coating composition is substantially free from boron.

\* \* \* \* \*